United States Patent
Yoshikawa (10) Patent No.: US 8,040,512 B2
(45) Date of Patent: Oct. 18, 2011

(54) INSPECTION DEVICE, INSPECTION METHOD, AND PROGRAM

(75) Inventor: Toru Yoshikawa, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/591,744

(22) Filed: Nov. 30, 2009

(65) Prior Publication Data

US 2010/0079758 A1 Apr. 1, 2010

Related U.S. Application Data

(63) Continuation of application No. PCT/JP2008/001481, filed on Jun. 10, 2008.

(30) Foreign Application Priority Data

Jun. 13, 2007 (JP) ................................. 2007-156443

(51) Int. Cl.
*G01J 4/00* (2006.01)
(52) U.S. Cl. ..................................... 356/369; 356/237.5
(58) Field of Classification Search .................. 356/369, 356/237.5
See application file for complete search history.

(56) References Cited

U.S. PATENT DOCUMENTS

| | | | |
|---|---|---|---|
| 2004/0150821 A1 | 8/2004 | Shibata et al. | |
| 2006/0072106 A1* | 4/2006 | Matsui et al. | ............. 356/237.5 |

FOREIGN PATENT DOCUMENTS

| | | |
|---|---|---|
| JP | A-2-189448 | 7/1990 |
| JP | A-2000-155099 | 6/2000 |
| JP | A-2003-302354 | 10/2003 |
| JP | A-2005-233869 | 9/2005 |
| WO | WO 2008/015973 A1 | 2/2008 |

OTHER PUBLICATIONS

International Preliminary Report on Patentability for International Application No. PCT/JP2008/001481, issued Dec. 17, 2009. (w/ Translation).
International Search Report for International Application No. PCT/JP2008/001481, issued Jul. 8, 2008.
Boye, Carol A., "Industry Survey on Non-visual Defect Detection," Process and Materials Characterization and Diagnostics in IC Manufacturing, *Proceedings of SPIE*, vol. 5041, 2003, pp. 173-182.
Kawai et al., Akitoshi, "Novel CD inspection technology leveraging a form birefringence in a Fourier space," Metrology, Inspection, and Process Control for Microlithography XXII, *Proc. of SPIE*, vol. 6922, 69221X, 2008, pp. 69221X-1-69221X-8.
Omori et al., Takeo, "Novel inspection technology for half pitch 55 nm and below," Metrology, Inspection, and Process Control for Microlithography XIX, *Proc. of SPIE*, vol. 5752, 2005, pp. 174-182.
Kawai et al., Akitoshi, "Novel CD Inspection Technology Leveraging a Form Birefringence in a Fourier space," 23 slides, 2008.

* cited by examiner

*Primary Examiner* — Roy Punnoose
(74) *Attorney, Agent, or Firm* — Oliff & Berridge, PLC (57) ABSTRACT

An illuminating optical system of an inspection device selects an arbitrary wavelength region from the light source, and epi-illuminates the sample via the polarizer and the objective lens. A detecting optical system includes an analyzer having a polarization plane intersected with a polarization direction of the polarizer. Then, the detecting optical system detects light from the sample via the objective lens and the analyzer, and acquires a Fourier image of a sample surface based on this light. An imaging section images the Fourier image. An analyzing section performs computation for processing for determining a notable area to be affected by a state of the pattern more than other areas in the Fourier image.

17 Claims, 13 Drawing Sheets

| FOURIER IMAGE | PATTERN LINE WIDTH(nm) | GRADATION VALUE OF R OF DIVIDED AREA Pm | GRADATION VALUE OF G OF DIVIDED AREA Pm | GRADATION VALUE OF B OF DIVIDED AREA Pm |
|---|---|---|---|---|
| $FI_1$ | 53.8 | 8 | 13 | 26 |
| $FI_2$ | 59.4 | 12 | 19 | 35 |
| $FI_3$ | 58.3 | 11 | 17 | 33 |
| $FI_4$ | 58.3 | 10 | 17 | 32 |
| $FI_5$ | 51.9 | 7 | 11 | 23 |
| ⋮ | ⋮ | ⋮ | ⋮ | ⋮ |
| $FI_n$ | 56.2 | 10 | 15 | 30 |

INSPECTION DEVICE, INSPECTION METHOD, AND PROGRAM

CROSS REFERENCE TO THE RELATED APPLICATIONS

This application is a continuation application of International Application PCT/JP2008/001481, filed Jun. 10, 2008, designating the U.S., and claims the benefit of priority from Japanese Patent Application No. 2007-156443, filed on Jun. 13, 2007, the entire contents of which are incorporated herein by reference.

BACKGROUND

1. Field

The present application relates to an inspection device, an inspection method, and a program for detecting a defect on a sample surface particularly in manufacturing process of a semiconductor element, a liquid crystal display element, and the like.

2. Description of the Related Art

Conventionally, various devices that detect defects, such as unevenness or flaws, on a sample surface utilizing diffracted light generated from a pattern formed on the surface of a semiconductor wafer or a liquid crystal substrate (generally, referred to as a "sample") have been proposed. Particularly, in recent years, with miniaturization of the semiconductor processes, there is a need for higher accuracy also in the defect control of samples.

As an example, Patent Document 1: Japanese Unexamined Patent Application Publication No. 2003-302354 discloses an electronic circuit component inspection device that selects a rejection candidate area of a substrate based on a difference between good reference color data, which is determined in advance, and color data of an inspection surface based on a color image.

Incidentally, in order to accurately observe patterns in the above-described defect inspection, the observation is preferably performed focusing on a portion noticeably exhibiting a pattern characteristic among the analysis results. However, it is complicated to identify the portion noticeably exhibiting a pattern characteristic in the analysis results, and there is still a need for improvement in this point.

The present application is intended to solve the above-described problem in the conventional technique. It is a proposition of the present invention to provide a means for easily identifying a portion noticeably exhibiting a pattern characteristic in the analysis results.

SUMMARY

An inspection device according to a first aspect of the present embodiment includes a stage for placing a sample having a pattern formed on a surface, an objective lens observing a pattern, an illuminating optical system, a detecting optical system, an imaging section, and an analyzing section. The illuminating optical system includes a light source and a polarizer. Then, the illuminating optical system selects an arbitrary wavelength region from the light source, and epi-illuminates the sample via the polarizer and the objective lens. The detecting optical system includes an analyzer having a polarization plane intersected with a polarization direction of the polarizer. Then, the detecting optical system detects light from the sample via the objective lens and the analyzer, and acquires a Fourier image of a sample surface based on the light. The imaging section images the Fourier image. The analyzing section performs computation processing for determining a notable area to be affected by a state of the pattern more than other areas in the Fourier image.

According to a second aspect of the present embodiment, in the first aspect of the present embodiment, the analyzing section computes a difference of a gradation occurring between a plurality of Fourier images for each position within an image based on the plurality of the Fourier images each having a different exposure condition of the pattern, and further determines the notable area from a magnitude of the difference of the gradation.

According to a third aspect of the present embodiment, in the second aspect of the present embodiment, the imaging section generates color data of the Fourier images. Moreover, the analyzing section computes the difference of the gradation for each of color components of the Fourier images, and determines the notable area based on data of one of the color components.

According to a fourth aspect of the present embodiment, in the first aspect of the present embodiment, the inspection device further includes a data input section receiving line width data of the pattern corresponding to the Fourier image. Moreover, the analyzing section computes a change rate between a gradation value of Fourier images and a line width of the pattern for each position within an image based on a plurality of the Fourier images each having a different exposure condition of the pattern, and determines the notable area based on a value of the change rate.

According to a fifth aspect of the present embodiment, in the fourth aspect of the present embodiment, the imaging section generates color data of the Fourier images. Moreover, the analyzing section computes the change rate for each of color components of the Fourier images, and determines the notable area based on data of one of the color components.

According to a sixth aspect of the present embodiment, in the fourth or fifth aspect of the present embodiment, the analyzing section further computes a correlation error of the line width for each position within an image, and determines the notable area based on a value of the change rate and the correlation error.

According to a seventh aspect of the present embodiment, in any of the first to sixth aspects of the present embodiment, the analyzing section performs at least one of a determination of whether the pattern in the sample is good or defective or a detection of change of the pattern based on data of the Fourier image corresponding to the notable area.

According to an eighth aspect of the present embodiment, in any of the fourth to sixth aspects of the present embodiment, the analyzing section determines an approximation for converting the gradation value into the line width at a time of computation of the change rate, and estimates the line width from the Fourier image based on the approximation.

Note that, implementations obtained by converting the configurations related to the above-described aspects of the present embodiment into an inspection method, and a program or the like for causing a computer to execute the inspection method are also effective as specific embodiments of the present embodiment.

According to the present invention, a notable area, which is affected by the state of a pattern more than other areas, can be determined based on a Fourier image obtained by imaging a pattern of a sample.

DETAILED DESCRIPTION OF THE EMBODIMENTS

Description of First Embodiment

Hereinafter, a configuration of a defect inspection device of a first embodiment will be described with reference to FIG. 1.

The defect inspection device includes a wafer stage 1, an objective lens 2, a half mirror 3, an illuminating optical system 4, a detecting optical system 5, an imaging section 6, and a control unit 7.

On the wafer stage 1, a wafer 8 (sample) of defect inspection target is placed with a pattern forming surface thereof facing upward. The wafer stage 1 can move in three axial directions of x, y, and z, the respective directions being perpendicular to each other (in FIG. 1, the vertical direction on the plane of the drawing is the z direction). Moreover, the wafer stage 1 can rotate around the z-axis.

The objective lens 2 for observing a pattern on the wafer 8 is disposed above the wafer stage 1. In the example of FIG. 1, the power of the objective lens 2 is set to 100 times. Then, the half mirror 3 is inclined and disposed above the objective lens 2. In FIG. 1, the illuminating optical system 4 is disposed on the left of the half mirror 3 and the detecting optical system 5 is disposed above the half mirror 3.

Figure 1:
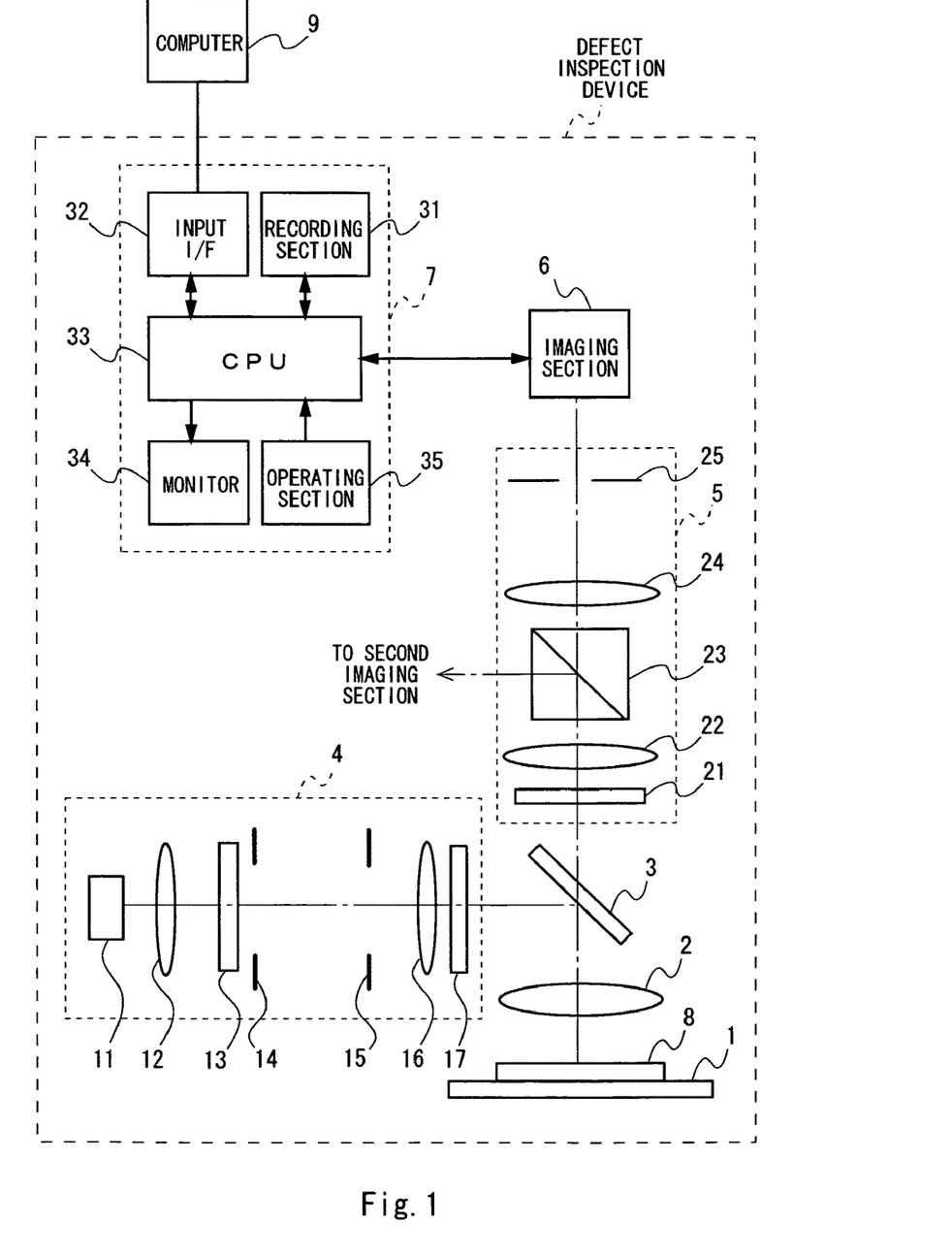
FIG. 1 is a schematic diagram of a defect inspection device of a first embodiment.

The illuminating optical system 4 includes, in the arrangement order from the left to the right of FIG. 1, a light source 11 (e.g., a white LED, a halogen lamp, or the like), a condenser lens 12, an illuminance equalization unit 13, an aperture stop 14, a field stop 15, a collimator lens 16, and a removable polarizer (polarizing filter) 17.

Here, light emitted from the light source 11 of the illuminating optical system 4 is guided to the aperture stop 14 and the field stop 15 via the condenser lens 12 and the illuminance equalization unit 13. The illuminance equalization unit 13 causes the light in an arbitrary wavelength region to pass therethrough by means of an interference filter. The above-described aperture stop 14 and field stop 15 are configured so that the size and position of an opening can be modified with respect to an optical axis of the illuminating optical system 4. Accordingly, the illuminating optical system 4, through operations of the aperture stop 14 and the field stop 15, can change the size and the position of an illumination area and adjust the aperture angle of illumination. Then, the light passing through the aperture stop 14 and the field stop 15 is collimated by the collimator lens 16, and thereafter passes through the polarizer 17 and is incident upon the half mirror 3.

The half mirror 3 reflects the light from the illuminating optical system 4 downward, and guides this light to the objective lens 2. Thereby, the wafer 8 is epi-illuminated with the light from the illuminating optical system 4 passing through the objective lens 2. On the other hand, the light epi-illuminated onto the wafer 8 is reflected by the wafer 8, and returns to the objective lens 2 again, and will pass through the half mirror 3 and be incident upon the detecting optical system 5.

The detecting optical system 5 includes, in the arrangement order from the lower side to the upper side of FIG. 1, a removable analyzer (polarizing filter) 21, a lens 22, a half prism 23, a Bertrand lens 24, and a field stop 25. The analyzer 21 of the detecting optical system 5 is disposed so as to be in a crossed nicols state relative to the polarizer 17 of the illuminating optical system 4. Since the polarizer 17 of the illuminating optical system 4 and the analyzer 21 of the detecting optical system 5 satisfy the crossed nicols condition, the light intensity observed by the detecting optical system 5 becomes close to zero unless the polarization principal axis is rotated by a pattern of the wafer 8.

Moreover, the half prism 23 of the detecting optical system 5 causes an incident light beam to branch in two directions. One of the light beams passing through the half prism 23 forms an image of the wafer 8 onto the field stop 25 via the Bertrand lens 24 while reproducing a luminance distribution on a pupil surface of the objective lens 2 onto an imaging surface of the imaging section 6. Namely, the imaging section 6 can take a Fourier-transformed image (Fourier image) of the wafer 8. Note that the field stop 25 can change the opening shape within a plane perpendicular to the optical axis of the detecting optical system 5. Therefore, through operation of the field stop 25, the imaging section 6 now can detect information in an arbitrary area of the wafer 8. Note that the other light beam passing through the half prism 23 is guided to a second imaging section (not shown) for taking an image not subjected to Fourier transform.

Here, taking a Fourier image (i.e., image of the pupil plane of the objective lens 2) in the defect inspection of the first embodiment is based on the following reasons. If an image taken by imaging a pattern of the wafer 8, as it is, is used in the defect inspection, it is impossible to optically detect a defect of the pattern when the pattern pitch is below the resolution of the inspection device. On the other hand, in the Fourier image, if a pattern of the wafer 8 has a defect, the symmetry of reflected light will break and a change will occur in the luminance, color, or the like between portions symmetrical to the optical axis of the Fourier image, due to structural doublerefraction. Therefore, even when the pattern pitch is below the resolution of the inspection device, the defect detection of a pattern becomes possible by detecting the above-described change in the Fourier image.

Figure 2:
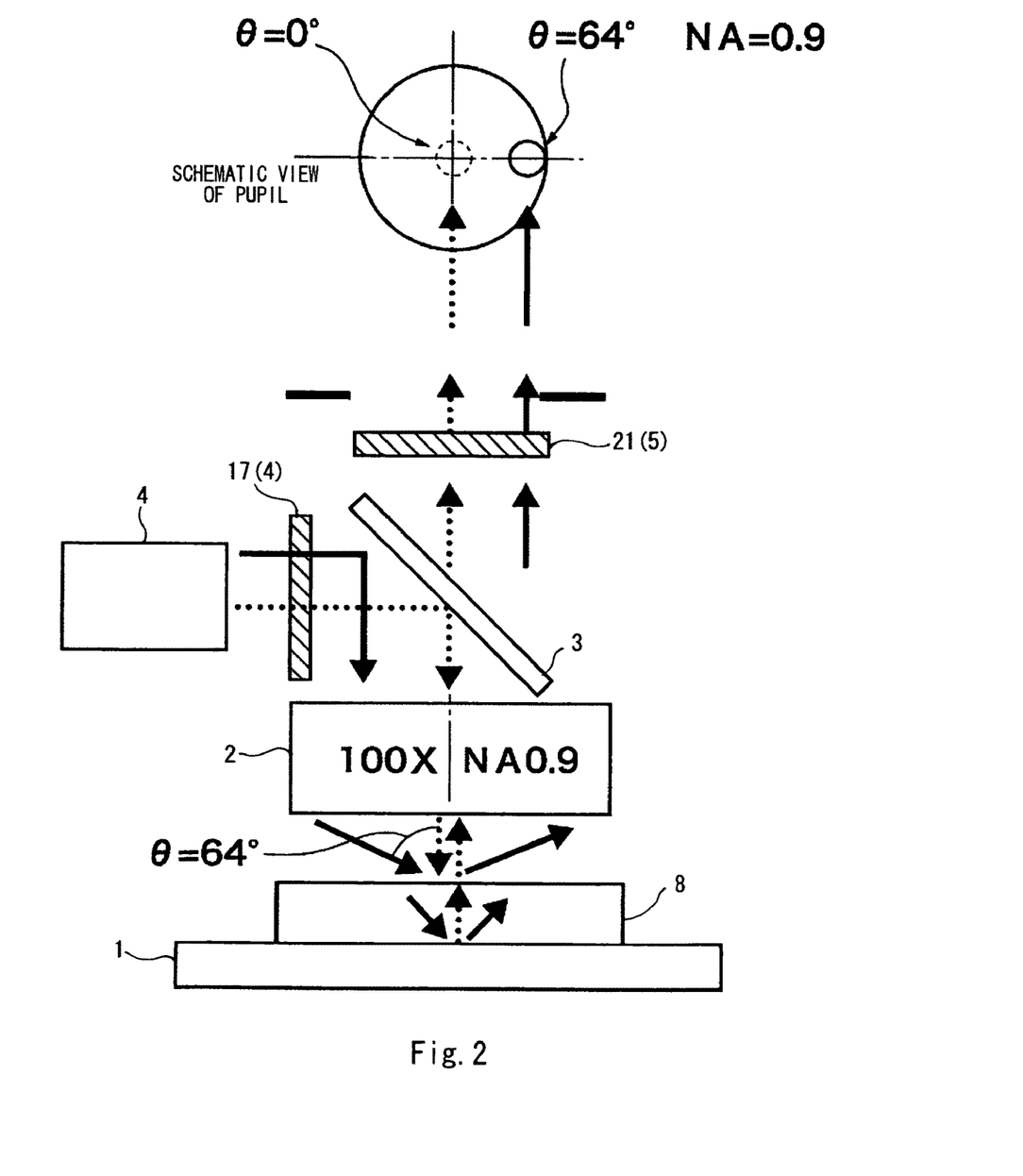
FIG. 2 is an explanatory view of a relationship between an incident angle of irradiation light upon a wafer and an imaging position within a pupil.

Furthermore, a relationship between the incident angle of irradiation light onto the wafer 8 and the imaging position within the pupil will be described with reference to FIG. 2. As shown by a dotted line in FIG. 2, when the incident angle of irradiation light onto the wafer 8 is 0°, the imaging position on the pupil is the center of the pupil. On the other hand, as shown by a solid line in FIG. 2, when the incident angle is 64° (equivalent to NA=0.9), the imaging position on the pupil is an outer edge portion of the pupil. Namely, the incident angle of irradiation light onto the wafer 8 corresponds to a position in the radial direction within the pupil, on the pupil. Moreover, the light formed at a position within the same radius from the optical axis within the pupil is the light incident upon the wafer 8 at the same angle.

Returning to FIG. 1, the imaging section 6 takes the above-described Fourier image by means of an image sensor having therein a color filter array of a Bayer array. Then, the imaging section 6 generates color data of R, G and B of the Fourier image by performing A/D conversion and various kinds of image processings on an output of the image sensor. This output of the imaging section 6 is coupled to the control unit 7. Note that FIG. 1 omits the illustration of the individual constituent element of the imaging section 6.

The control unit 7 performs general control of the defect inspection device. The control unit 7 includes a recording section 31 for recording data of a Fourier image, an input I/F 32, a CPU 33 for executing various kinds of computations, a monitor 34, and an operating section 35. The recording section 31, the input I/F 32, the monitor 34, and the operating section 35 are coupled to the CPU 33, respectively.

Here, the CPU 33 of the control unit 7 analyzes a Fourier image by executing a program, and determines a notable area affected by the state of the pattern more than other areas in the Fourier image. Moreover, the input I/F 32 includes a connector for coupling a recording medium (not shown), and a connection terminal for coupling to an external computer 9. Then, the input I/F 32 reads data from the above-described recording medium or computer 9.

Figure 3:
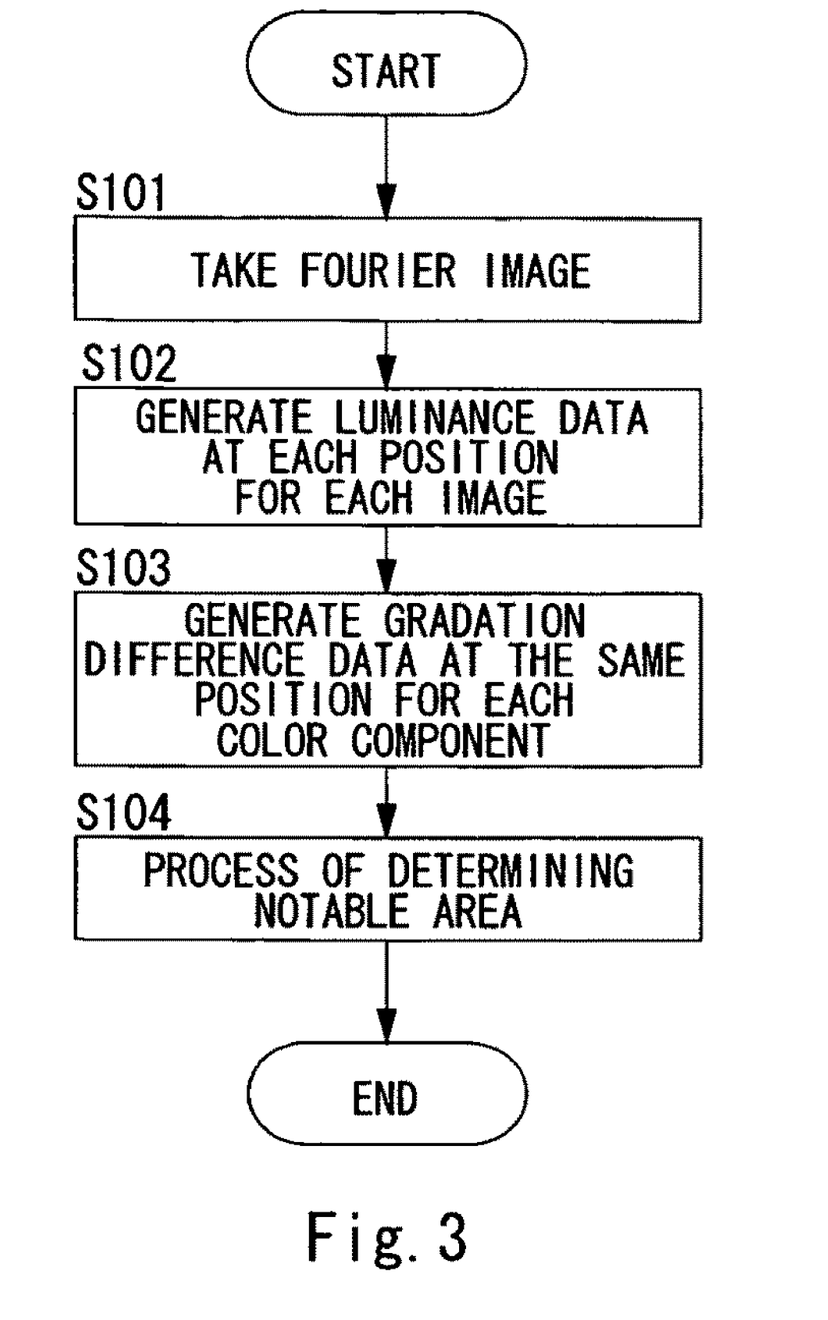
FIG. 3 is a flow chart illustrating how to determine a notable area in the first embodiment.

Next, an example of how to determine a notable area when inspecting a defect according to the first embodiment will be described with reference to a flow chart of FIG. 3. In the first embodiment, an example will be described, in which a notable area in the defect inspection is determined utilizing one wafer 8 having a plurality of patterns of the same shape formed therein, each pattern having a different exposure condition (focus/dose).

Step 101: the CPU 33 of the control unit 7 causes the imaging section 6 to take each Fourier image for a predetermined position of each pattern on the wafer 8. Thereby, for a pattern of the same shape, the color data of a plurality of Fourier images each having a different exposure condition will be recorded in the recording section 31 of the control unit 7. Note that, in the following description, for sake of simplicity, when discriminating the respective Fourier images, description will be given with symbol FI attached.

Step 102: the CPU 33 generates luminance data of R, G and B, respectively, for each position on an image, for each Fourier image. Hereinafter, how to determine the above-described luminance data is specifically described taking a Fourier image $FI_1$ of the first frame as an example.

Figure 4:
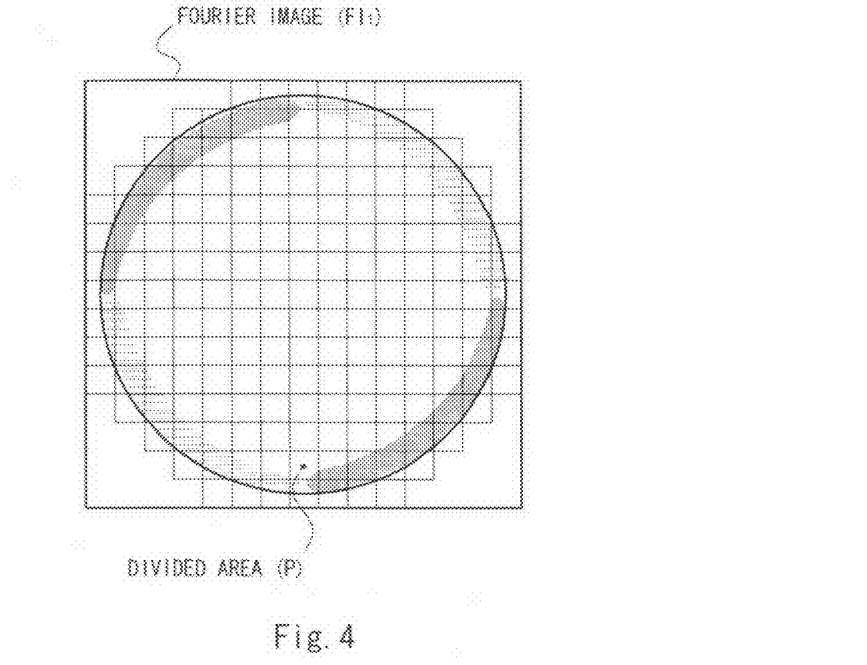
FIG. 4 shows an example of a Fourier image divided into areas.

(1) The CPU 33 divides the Fourier image $FI_1$ into a plurality of tetragonal lattice-like areas. FIG. 4 shows an example of the Fourier image divided into areas. Note that, in the following description, for sake of simplicity, when discriminating the divided areas on the Fourier image, description will be given with symbol P attached.

(2) The CPU 33 computes an average of luminance values of R, G and B for each of the colors, for each divided area of the Fourier image $FI_1$. Thereby, for each divided area of $FI_1$, luminance data indicative of the gradation for each color component of R, G and B is generated, respectively.

Then, the CPU 33 repeats the above steps of (1) and (2) in the respective Fourier images. Thereby, the luminance data of R, G and B for each divided area will be generated, respectively, in each of the Fourier images ($FI_1$ to $FI_n$) from the first frame to the n-th frame.

Step 103: the CPU 33 generates gradation difference data indicative of a difference of gradation between the Fourier images ($FI_1$ to $FI_n$) in the same divided area, for each color component of R, G and B.

Hereinafter, the computation in S103 is specifically described taking an arbitrary divided area $P_m$ on the Fourier image FI as an example.

Figure 5:
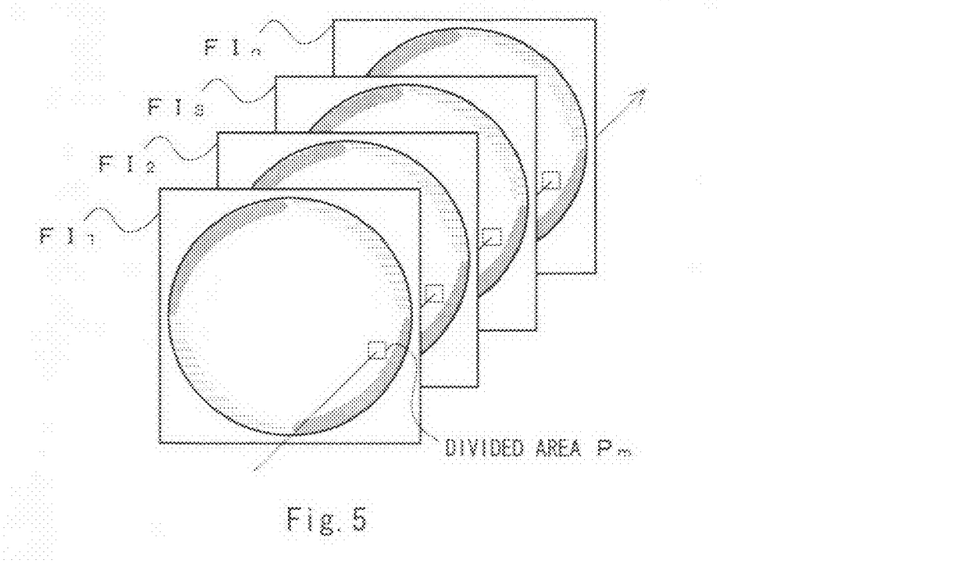
FIG. 5 is a schematic view showing an extraction state of luminance data in S103.
Figure 6:
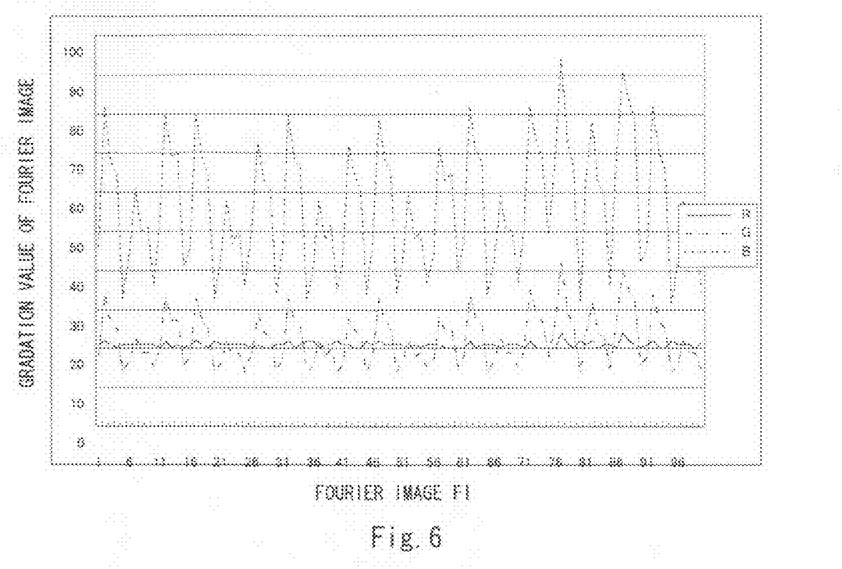
FIG. 6 is a graph showing the gradation values of R, G, and B of the luminance data in a divided area $P_m$.

First, for each of the Fourier images ($FI_1$ to $FI_n$), the CPU 33 extracts luminance data (those computed in S102) of each color component in the divided area $P_m$, respectively (see FIG. 5). Next, the CPU 33 compares the gradation values in the divided area $P_m$ for each color component, respectively. FIG. 6 is a graph showing the gradation values of R, G and B of the luminance data in the divided area $P_m$. Note that, in FIG. 6, the horizontal axis represents the number of the Fourier image FI while the vertical axis represents the gradation value of each Fourier image.

Furthermore, the CPU 33 extracts the maximum value and the minimum value for each of R, G and B among the gradation values of luminance data corresponding to the divided area $P_m$. Subsequently, the CPU 33 computes a difference value between the above-described maximum value and minimum value for each color component of R, G and B. Thereby, the gradation difference data indicative of a difference of gradation between Fourier images in the divided area $P_m$ is generated for each color component of R, G and B.

Then, the CPU 33 repeats the above steps as many times as the number of all the divided areas. Thereby, the gradation difference data for each of R, G and B will be generated, respectively, in all the divided areas of the Fourier image.

Step 104: the CPU 33 determines a notable area affected by the state of the pattern more than other areas of the divided areas of the Fourier image, based on the gradation difference data determined in S103.

Figure 7:
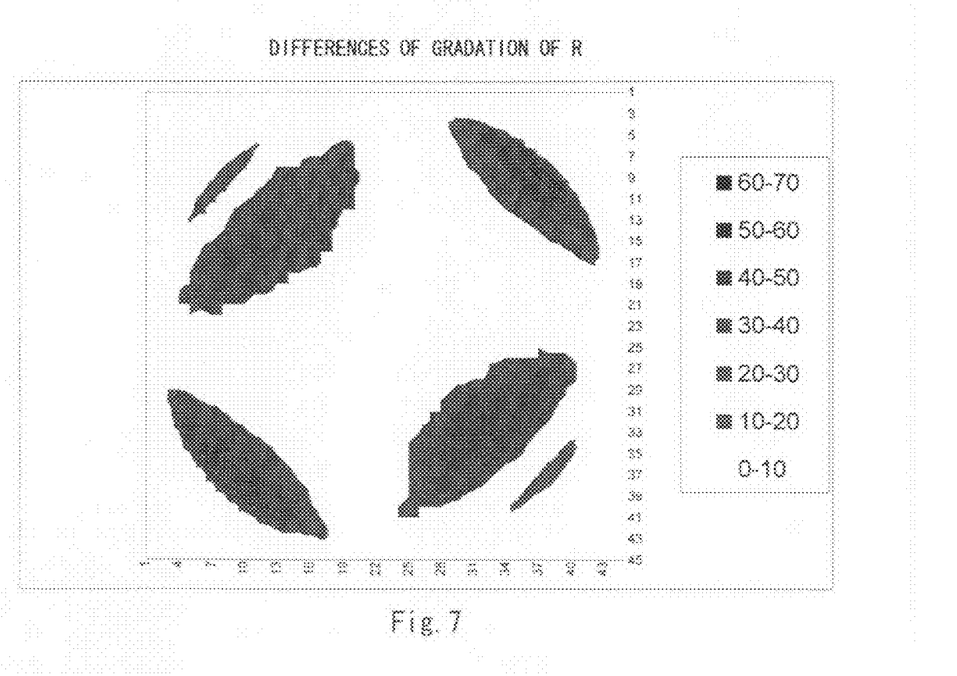
FIG. 7 shows a distribution state of differences of gradation of R in a Fourier image.
Figure 8:
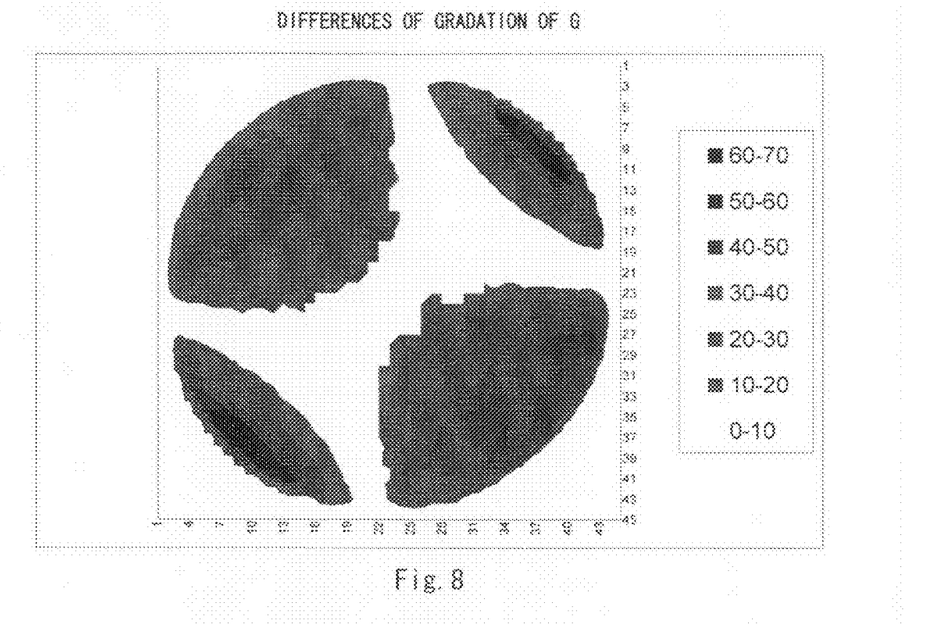
FIG. 8 shows a distribution state of differences of gradation of G in the Fourier image.
Figure 9:
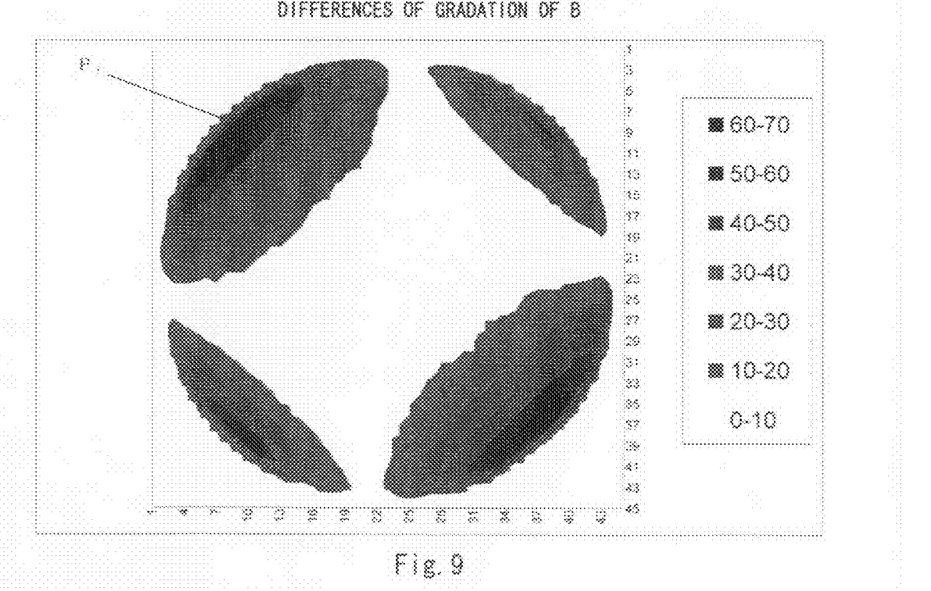
FIG. 9 shows a distribution state of differences of gradation of B in the Fourier image.

FIG. 7 to FIG. 9 show distribution states of differences of gradation in each divided area of the Fourier image, for each color component. In the above example, for a difference of gradation of the luminance between Fourier images, the value of B in the divided area $P_1$ is the maximum (see FIG. 9). Therefore, the CPU 33 in S104 determines the divided area $P_1$ as the notable area, and performs defect inspection to be described later, based on the gradation value of B in the divided area $P_1$. Here, the position of the notable area in the Fourier image varies according to a pattern of the wafer 8. Moreover, a color component with an increased difference of gradation has a high gradation value, which may be enhanced by interference of thin films on the wafer 8. Now, the description of the flow chart of FIG. 3 is complete.

Then, the CPU 33 performs defect inspection of a pattern of the wafer 8 by analyzing the Fourier image paying attention to the notable area and the color component that have been determined by the above-described method. Here, in the above-described notable area in the Fourier image, defect inspection of a pattern can be performed with high accuracy because a change is likely to appear in the gradation of a predetermined color component even with a slight change in the pattern condition.

Figure 10:
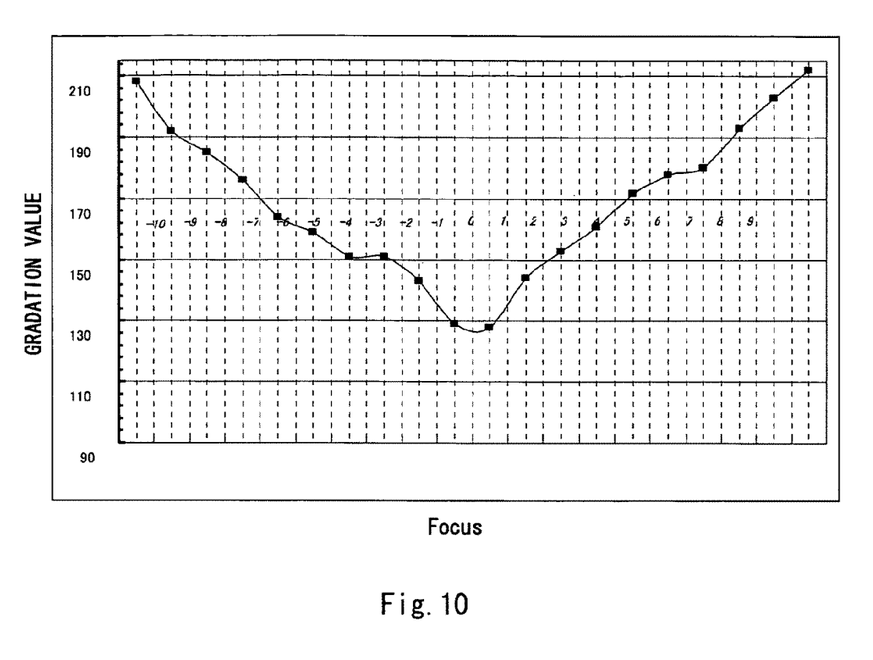
FIG. 10 is a graph showing a correlation between a focus of a pattern and a gradation value of a Fourier image.

As an example, if a correlation between the exposure condition of a pattern and the gradation value is found in advance, then the CPU 33 can, when analyzing a Fourier image taken by imaging a pattern of defect inspection target, easily perform defect inspection of the pattern based on data (in the above-described example, the gradation value of B in the divided area $P_1$) of a predetermined color component in a notable area. Here, in the Fourier image taken by imaging a pattern of the same shape with different focus conditions, respectively, FIG. 10 shows a correlation between the focus condition of a pattern and the gradation value of a Fourier image. If the control unit 7 can use data for judgment corresponding to FIG. 10, then the CPU 33 can detect a defect of the pattern on the wafer 8 by comparing the gradation value of a predetermined color component in a notable area of the Fourier image with the gradation values in a non-defective range of the focus condition in the data for judgment.

Moreover, at the time of analysis of a plurality of Fourier images of defect inspection target, the CPU 33 can also perform change detection of a pattern of the wafer 8 by extracting an image having a change no less than a threshold value in the gradation of a predetermined color component in a notable area.

Description of Second Embodiment

Figure 11:
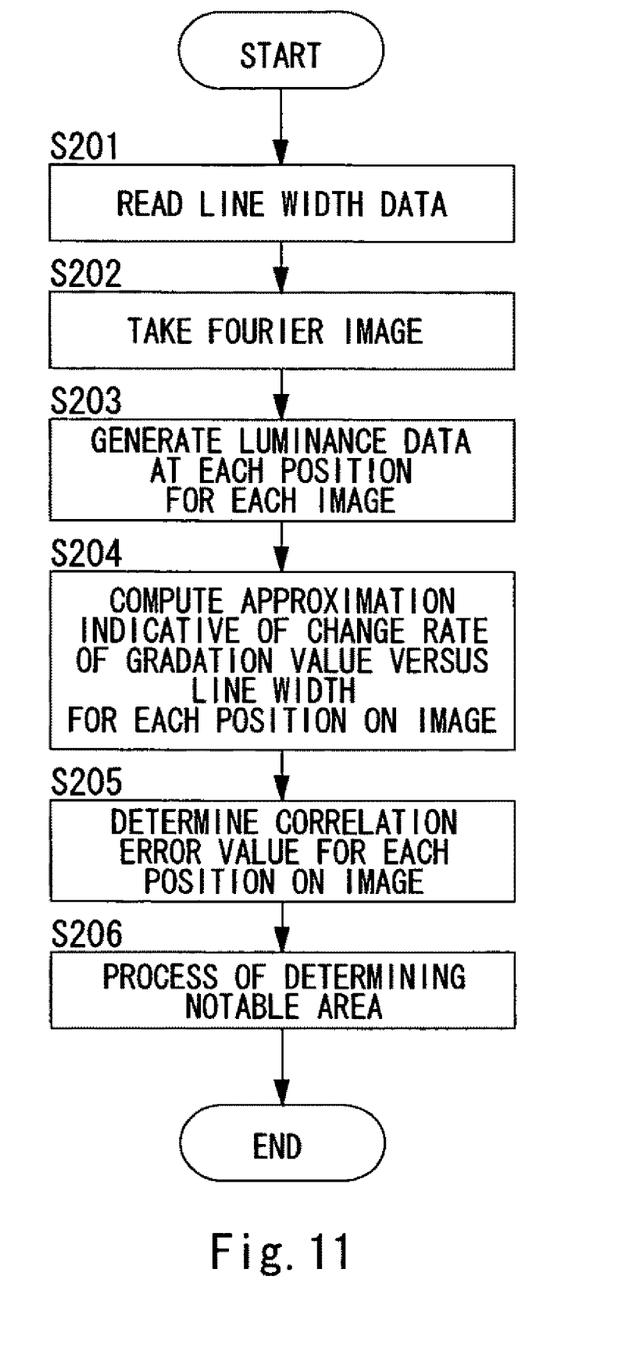
FIG. 11 is a flow chart illustrating how to determine a notable area in a second embodiment.

FIG. 11 is a flow chart illustrating an example of how to determine a notable area at the time of defect inspection according to a second embodiment. Here, because the configuration of a defect inspection device of the second embodiment is common with the defect inspection device of the first embodiment shown in FIG. 1, the duplicated description is omitted.

In the second embodiment, a notable area in defect inspection is determined based on the Fourier image of each pattern and the data of a line width for each pattern, using the same wafer 8 as that of the first embodiment. Note that, for the data of a line width corresponding to the above-described pattern, the data measured with a line width measuring device, such as a scatterometer or a scanning electron microscope (SEM), is used, for example.

Step 201: the CPU 33 reads and acquires a data group of line widths corresponding to the respective patterns from the input I/F 32, for the wafer 8. Note that the data group of line widths read into the control unit 7 is recorded in the recording section 31.

Step 202: the CPU 33 causes the imaging section 6 to take each Fourier image for each pattern on the wafer 8. Note that, since this step corresponds to S101 of FIG. 3, the duplicated description is omitted.

Step 203: the CPU 33 generates luminance data of R, G and B, respectively, for each position on an image, for the respective Fourier images. Note that, since this step corresponds to S102 of FIG. 3, the duplicated description is omitted.

Step 204: the CPU 33 determines an approximation indicative of a change rate of the gradation value of a Fourier image versus the line width of a pattern, in each divided area (S203) on a Fourier image. Note that the CPU 33 in S204 computes the above-described approximation for each color component of R, G and B, respectively, in one divided area.

Hereinafter, the computation in S204 will be specifically described taking an arbitrary divided area $P_m$ on the Fourier image FI as an example.

Figure 12:
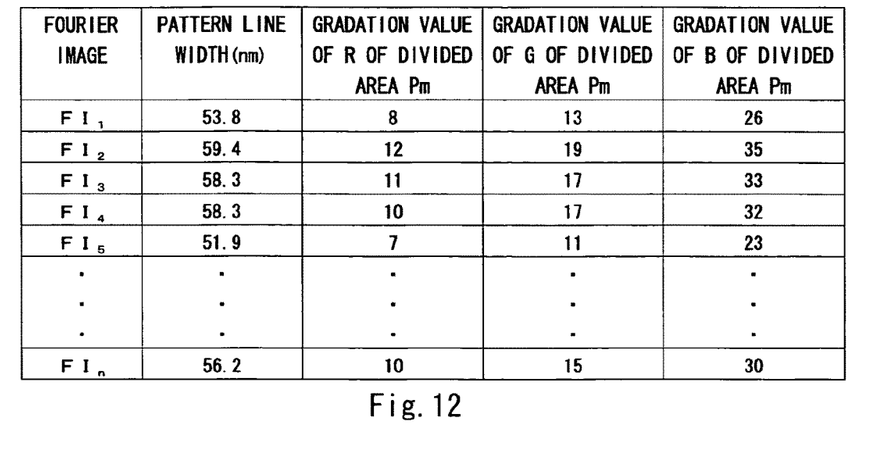
FIG. 12 shows an example of a correspondence between a line width of a pattern corresponding to each Fourier image and gradation values of R, G, and B in the divided area $P_m$.

(1) Firstly, the CPU 33 reads data of a line width of a pattern corresponding to each of the Fourier images ($FI_1$ to $FI_n$), from the recording section 31. Moreover, the CPU 33 extracts luminance data (the data determined in S203) of each color component in the divided area $P_m$ in each of the Fourier images ($FI_1$ to $FI_n$), respectively. Then, the CPU 33 determines a correspondence between the line width of a pattern and the gradation value in the divided area $P_m$, for each of the Fourier images ($FI_1$ to $FI_n$). Note that FIG. 12 shows an example of the correspondence between the line width of a pattern corresponding to each of the Fourier images ($FI_1$ to $FI_n$) and the gradation values of R, G and B in the divided area $P_m$.

(2) Secondly, the CPU 33 computes an approximation indicative of a change rate of the gradation value of a Fourier image versus the line width of a pattern, based on the data of a correspondence between the line width and the gradation value determined in (1).

Figure 13:
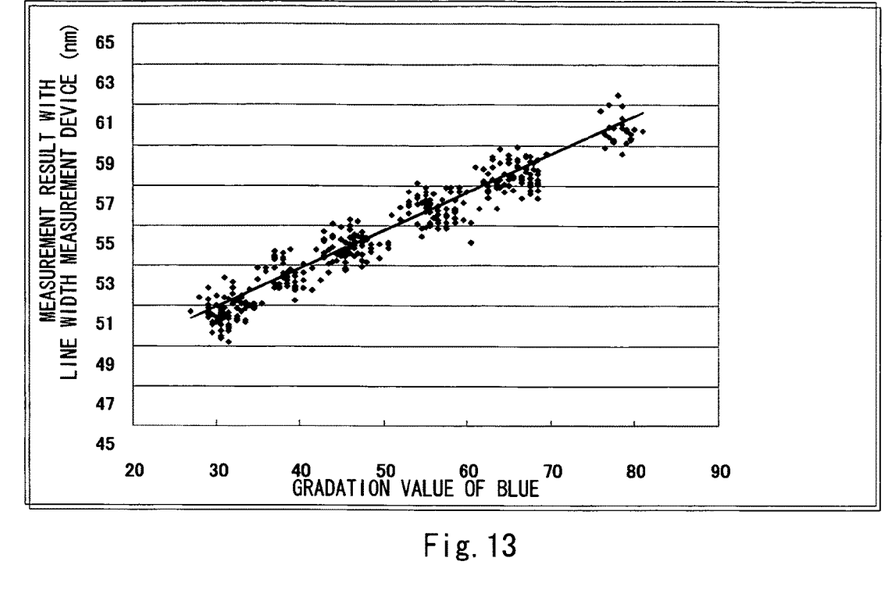
FIG. 13 is a graph showing the line widths of a pattern and the gradation values of B in the divided area $P_m$.

Here, the computation of the approximation corresponding to the gradation value of B in the divided area $P_m$ is described. FIG. 13 shows a graph of the line width of a pattern and the gradation value of B in the divided area $P_m$. In FIG. 13, the horizontal axis represents the gradation value of B in the divided area $P_m$ while the vertical axis represents the line width of a pattern. Note that, in FIG. 13, one point per one Fourier image is plotted on the graph.

As apparent also from FIG. 13, the line width of a pattern and the gradation value of a Fourier image linearly proportional to each other, which well agrees with the first-order approximation. Therefore, the CPU 33 computes the following Equation 1 from the data of a correspondence between the line width of a pattern and the gradation value of B in the divided area $P_m$ by using the least square method.

$$y=ax+b \quad (1)$$

In the above Equation 1, "y" denotes the line width of a pattern corresponding to each Fourier image. "x" denotes the gradation value of B in the divided area $P_m$. "a" represents a coefficient obtained by dividing the amount of change in the line width of a pattern by the amount of change in the gradation value of B. "b" represents the value of a y-intercept. Here, the absolute value of the above-described coefficient "a" is equal to a reciprocal (a reciprocal of the detection sensitivity of the state of a pattern) of the gradation change relative to the change in the line width of a pattern. Namely, as the absolute value of the coefficient "a" decreases, the gradation change of the Fourier image increases even if the difference in line widths is the same, and therefore the detection sensitivity of the state of a pattern will improve.

Through the above-described steps, the CPU 33 can determine the approximation corresponding to the gradation value of B in the divided area $P_m$. Of course, the CPU 33 also computes the approximations corresponding to the gradation values of R and G in the divided area $P_m$, in the same steps as those described above. Subsequently, the CPU 33 computes the approximation corresponding to each of the gradation values of R, G and B in all the divided areas on a Fourier image, respectively.

Step 205: the CPU 33 determines a correlation error between the approximation obtained in S204 and the line width of a pattern for each color component, in each divided area (S203) on a Fourier image.

First, the CPU 33 generates the data of a deviation between the line width corresponding to each of the Fourier images ($FI_1$ to $FI_n$) and the line width derived from the approximation (S204). Of course, the CPU 33 generates the above-described deviation data for each color component of R, G and B in each divided area, respectively. Then, the CPU 33 computes a standard deviation for each color component of R, G and B of each divided area from the above-described deviation data, and regards this value as a correlation error.

Step 206: the CPU 33 determines a notable area affected by the state of the pattern more than other areas among the divided areas of the Fourier image, based on the coefficient "a" (the reciprocal of the detection sensitivity of the state of a pattern) determined in S204 and the correlation error determined in S205. Namely, the CPU 33 sets the above-described notable area from the divided areas having a small absolute value of the coefficient "a" and having a sufficiently small correlation error. As an example, the CPU 33 performs scoring of each of the divided areas according to the smallness of the absolute value of the coefficient "a" and the smallness of the correlation error, and determines a notable area based on the result of this scoring.

Figure 14:
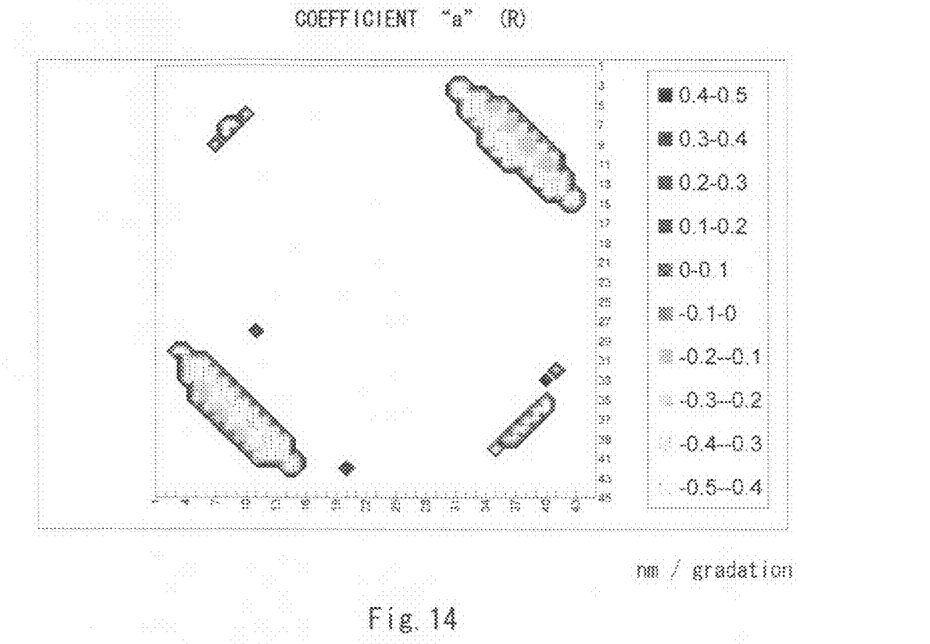
FIG. 14 shows a distribution state of values of a coefficient "a" corresponding to R in a Fourier image.
Figure 15:
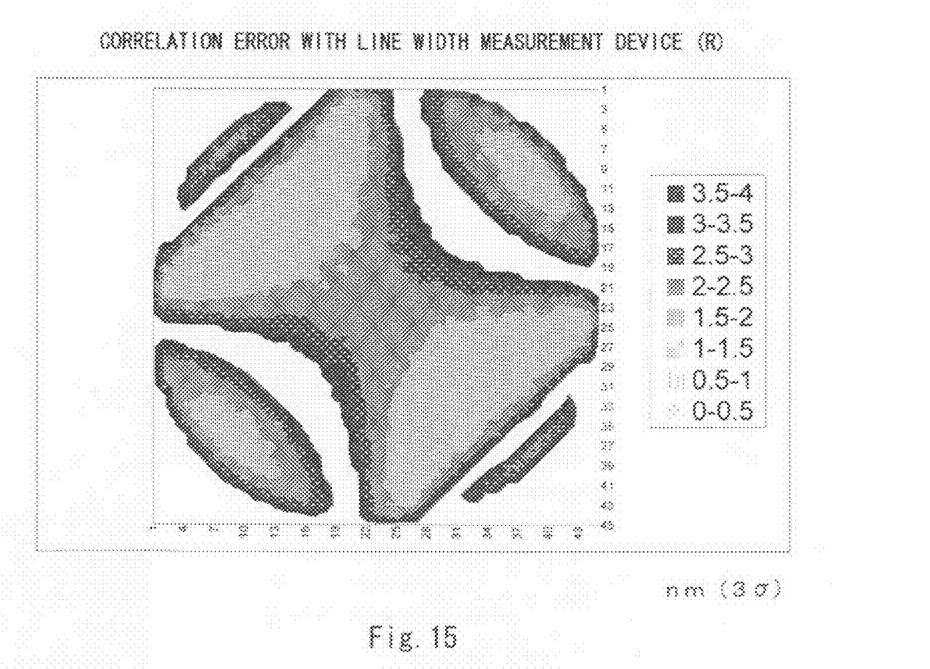
FIG. 15 shows a distribution state of values of a correlation error corresponding to R in the Fourier image.
Figure 16:
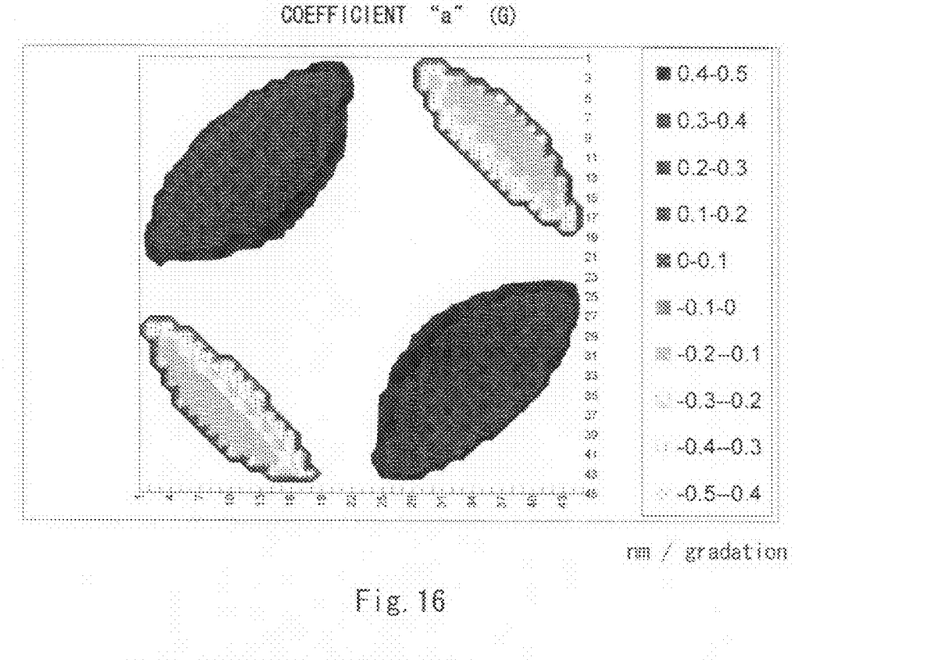
FIG. 16 shows a distribution state of values of the coefficient "a" corresponding to G in the Fourier image.
Figure 17:
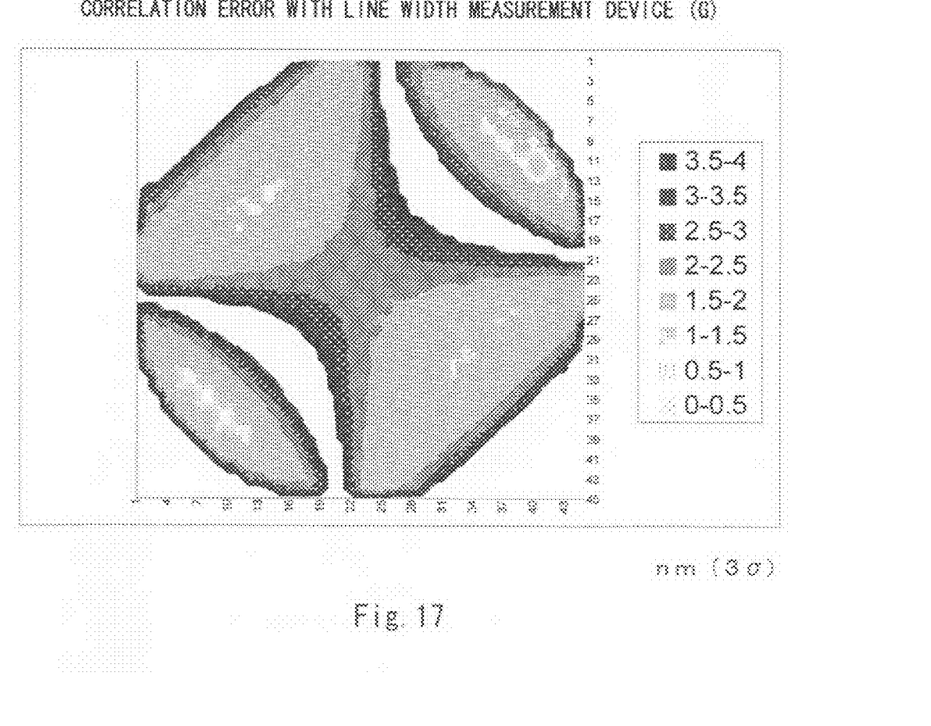
FIG. 17 shows a distribution state of values of a correlation error corresponding to G in the Fourier image.
Figure 18:
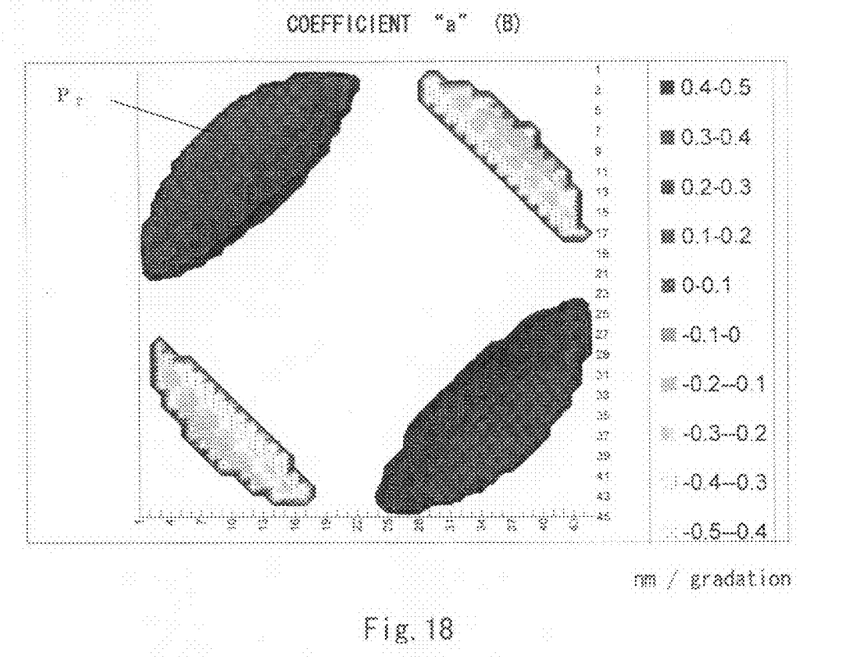
FIG. 18 shows a distribution state of values of the coefficient "a" corresponding to B in the Fourier image.
Figure 19:
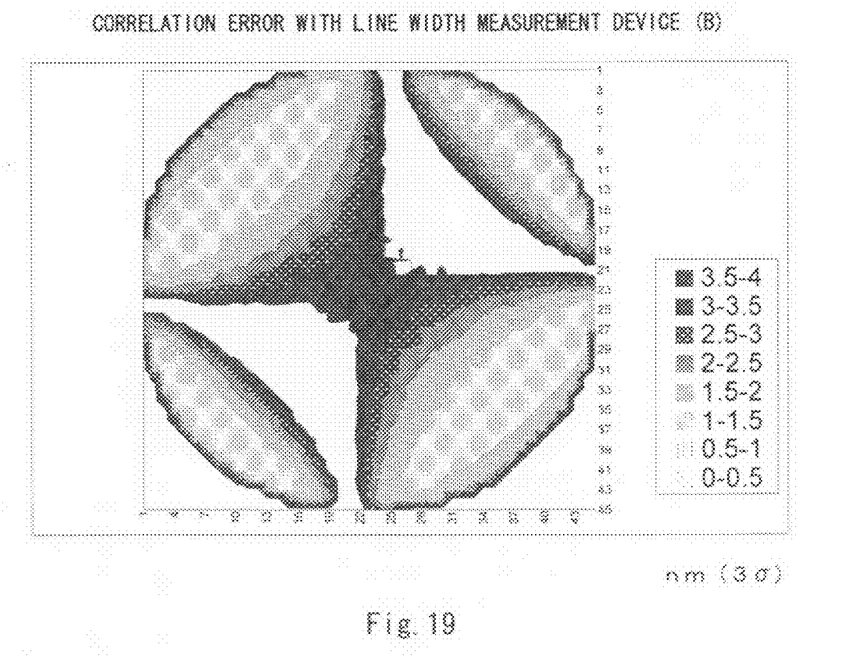
FIG. 19 shows a distribution state of values of a correlation error corresponding to B in the Fourier image.

FIG. 14, FIG. 16, and FIG. 18 are graphs each illustrating a distribution state of the values of the coefficient "a" of the approximation in a Fourier image for each color component. Moreover, FIG. 15, FIG. 17, and FIG. 19 are graphs each illustrating a distribution state of the values of the correlation error in the Fourier image for each color component. In the above-described example, the absolute value of the coefficient "a" of the approximation corresponding to the gradation value of B in the divided area $P_2$ is the minimum. Moreover, for the gradation value of B in the divided area $P_2$, the value of the correlation error is also a relatively small value. Therefore, the CPU 33 in S206 determines the divided area $P_2$ as the notable area, and performs defect inspection to be described later, based on the gradation value of B in the divided area $P_2$. Now, the description of the flow chart of FIG. 11 is complete.

Then, the CPU 33 performs defect inspection or change detection of a pattern of the wafer 8 by analyzing a Fourier image paying attention to the notable area and the color component which have been determined using the above-described method. Particularly, in the second embodiment, the notable area is determined paying attention also to the correlation error of the line width of a pattern, and therefore the defect inspection or the like of a pattern can be conducted more accurately. Note that the techniques for the defect inspection or change detection of a pattern in the second embodiment are almost the same as those of the case of the first embodiment, so the duplicated description is omitted.

Moreover, the CPU 33 in the second embodiment can estimate the line width of a pattern to be inspected from a Fourier image obtained by imaging the same pattern as the one used in determining a notable area. In this case, the CPU 33 acquires the gradation value (the gradation value of B in the divided area $P_2$, in the above-described example) of a predetermined color component of the notable area from a Fourier image to be inspected. Then, the CPU 33 estimates the line width of a pattern from the above-described gradation value based on the approximation determined in S204 and S206. Accordingly, in the second embodiment, estimation of the line width of a pattern can be performed simultaneously with defect inspection, based on a Fourier image, and therefore the workability in the inspection steps of the wafer 8 can be improved significantly.

Since the estimation of a line width of the second embodiment is performed based on the gradation of a pattern after Fourier transform, the estimate value of the above-described line width is equal to the one obtained by averaging the line widths of a pattern of an arbitrary area of the wafer 8, the arbitrary area being determined by the field stop 25. Accordingly, in the case of the second embodiment, the measurement error of a pattern is reduced significantly as compared with the measurement result of SEM.

Moreover, burning or the like of a pattern due to the electron beam may occur in the line width measurement using SEM, while in the defect inspection device of the second embodiment such an inconvenience will not occur. Furthermore, in the line width measurement using a scatterometer, a great amount of time is required for the setup prior to the measurement, while according to the second embodiment, estimation of the line width of a pattern can be easily performed almost without complicated setting works.

Note that, the first-order approximation is used as the approximation in this embodiment, but not limited thereto, and logarithmic approximation, exponential approximation, or polynomial approximation may be used.

Supplementary Notes on the Embodiments (1) In the above-described embodiments, an example has been described, in which the CPU 33 of a defect inspection device performs computation for determining a notable area. However, in the present invention, for example, the data of a Fourier image from the defect inspection device may be loaded into the computer 9 in FIG. 1, which executes the computation for determining a notable area.

(2) The CPU 33 in the above-described embodiments may perform defect inspection or the like of a pattern with reference to a plurality of notable areas and color components, instead of limiting the number of notable areas and the number of the color components to one.

(3) In the above-described embodiments, an example has been described, in which the CPU 33 determines a notable area and a color component. However, for example, the CPU 33 may display the computation results, such as the difference of gradation in each divided area, on the monitor 34, so that the CPU 33 may determine the notable area and the color component in response to the operation of an operator.

(4) In the above-described embodiments, an example has been described, in which the CPU 33 determines a notable area based on the color data of a Fourier image. However, in the present invention, the notable area may be determined using the data of a Fourier image in grayscale.

(5) In the above-described embodiments, an example has been described, in which the CPU 33 determines a notable area based on the data of a Fourier image of an RGB color space. However, in the present invention, for example, the data of a Fourier image may be converted into data of an HIS color space, so that the CPU 33 may perform computation.

(6) In the above-described embodiments, an example has been described, in which a polarizer and an analyzer are arranged in the crossed nicols state. However, in the present invention, polarization surfaces of the polarizer and the analyzer may be intersected with each other, and the arrangement thereof is not limited to the one satisfying the crossed nicols condition.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. An inspection device, comprising:
 a stage for placing a sample having a pattern formed on a surface;
 an objective lens observing the pattern;
 an illuminating optical system including a light source and a polarizer, selecting an arbitrary wavelength region from the light source, and epi-illuminating the sample via the polarizer and the objective lens;
 a detecting optical system including an analyzer having a polarization plane intersected with a polarization direction of the polarizer, detecting light from the sample via the objective lens and the analyzer, and acquiring a Fourier image of a sample surface based on the light;
an imaging section imaging the Fourier image; and
an analyzing section performing computation processing for determining a notable area to be affected by a state of the pattern more than other areas in the Fourier image.

2. The inspection device according to claim 1, wherein the analyzing section computes a difference of a gradation occurring between a plurality of Fourier images for each position within an image based on the plurality of the Fourier images each having a different exposure condition of the pattern, and further determines the notable area from a magnitude of the difference of the gradation.

3. The inspection device according to claim 2, wherein the imaging section generates color data of the Fourier images, and
the analyzing section computes the difference of the gradation for each of color components of the Fourier images, and determines the notable area based on data of one of the color components.

4. The inspection device according to claim 1, further comprising
a data input section receiving line width data of the pattern corresponding to the Fourier image, wherein
the analyzing section computes a change rate between a gradation value of Fourier images and a line width of the pattern for each position within an image based on a plurality of the Fourier images each having a different exposure condition of the pattern, and determines the notable area based on a value of the change rate.

5. The inspection device according to claim 4, wherein the imaging section generates color data of the Fourier images, and
the analyzing section computes the change rate for each of color components of the Fourier images, and determines the notable area based on data of one of the color components.

6. The inspection device according to claim 4, wherein the analyzing section further computes a correlation error of the line width for each position within an image, and determines the notable area based on a value of the change rate and the correlation error.

7. The inspection device according to claim 1, wherein the analyzing section performs at least one of a determination and a detection based on data of the Fourier image corresponding to the notable area, in which the determination determines whether the pattern in the sample is good or defective and the detection detects change of the pattern.

8. The inspection device according to claim 4, wherein the analyzing section determines an approximation for converting the gradation value into the line width at a time of computation of the change rate, and estimates the line width from the Fourier image based on the approximation.

9. An inspection method using an inspection device including
a stage for placing a sample having a pattern formed on a surface,
an objective lens observing the pattern,
an illuminating optical system including a light source and a polarizer, selecting an arbitrary wavelength region from the light source, and epi-illuminating the sample via the polarizer and the objective lens, and
a detecting optical system including an analyzer having a polarization plane intersected with a polarization direction of the polarizer, detecting light from the sample via the objective lens and the analyzer, and acquiring a Fourier image of a sample surface based on the light, the inspection method comprising:
an image data acquisition step acquiring data of the Fourier image; and
an analysis step determining a notable area to be affected by a state of the pattern more than other areas in the Fourier image.

10. The inspection method according to claim 9, wherein the analysis step includes computing a difference of a gradation occurring between a plurality of Fourier images for each position within an image based on the plurality of the Fourier images each having a different exposure condition of the pattern, and determining the notable area from a magnitude of the difference of the gradation.

11. The inspection method according to claim 10, wherein the image data acquisition step includes acquiring color data of the Fourier images, and
the analysis step includes computing the difference of the gradation for each of color components of the Fourier images, and determining the notable area based on data of one of the color components.

12. The inspection method according to claim 9, further comprising
acquiring line width data of the pattern corresponding to the Fourier image prior to the analysis step, wherein
the analysis step includes computing a change rate between a gradation value of Fourier images and a line width of the pattern for each position within an image based on a plurality of the Fourier images each having a different exposure condition of the pattern, and determining the notable area based on a value of the change rate.

13. The inspection method according to claim 12, wherein the image data acquisition step includes acquiring color data of the Fourier images, and
the analysis step includes computing the change rate for each of color components of the Fourier images, and determining the notable area based on data of one of the color components.

14. The inspection method according to claim 12, wherein the analysis step includes further computing a correlation error of the line width for each position within an image, and determining the notable area based on a value of the change rate and the correlation error.

15. The inspection method according to claim 9, further comprising,
a determination step performing at least one of a determination and a detection based on data of the Fourier image corresponding to the notable area, in which the determination determines whether the pattern in the sample is good or defective and the detection detects change of the pattern.

16. The inspection method according to claim 12, wherein the analysis step further comprises determining an approximation for converting the gradation value into the line width at a time of computation of the change rate, the inspection method further comprising estimating the line width from the Fourier image based on the approximation.

17. A computer readable storage medium storing a program causing a computer to execute the image data acquisition step and the analysis step in the inspection method according to claim 9.

* * * * *